(12) United States Patent
Brouwer

(10) Patent No.: US 8,593,626 B2
(45) Date of Patent: Nov. 26, 2013

(54) METHOD FOR INSPECTING THE INSIDE OF A NARROW HOSE OR TUBE PARTICULARLY FOR MEDICAL USE

(75) Inventor: Egbert Anne Martijn Brouwer, Zoetermeer (NL)

(73) Assignee: Nederlandse Organisatie voor toegepast-natuurwetenschappelijk onderzoek TNO, Delft (NL)

( * ) Notice: Subject to any disclaimer, the term of this patent is extended or adjusted under 35 U.S.C. 154(b) by 236 days.

(21) Appl. No.: 13/139,970

(22) PCT Filed: Dec. 17, 2009

(86) PCT No.: PCT/NL2009/050773
§ 371 (c)(1),
(2), (4) Date: Sep. 29, 2011

(87) PCT Pub. No.: WO2010/071429
PCT Pub. Date: Jun. 24, 2010

(65) Prior Publication Data
US 2012/0019807 A1    Jan. 26, 2012

(30) Foreign Application Priority Data
Dec. 17, 2008  (EP) .................................... 08171980

(51) Int. Cl.
*G01N 21/00* (2006.01)
(52) U.S. Cl.
USPC .................. 356/241.1; 356/240.1; 356/241.4
(58) Field of Classification Search
USPC .................... 356/237.1–241.6, 242.1–243.8, 356/426–431, 600–640
See application file for complete search history.

(56) References Cited

U.S. PATENT DOCUMENTS 4,559,813 A * 12/1985 Brekelmans ................. 73/61.69
5,747,794 A    5/1998 Malchesky
(Continued)

FOREIGN PATENT DOCUMENTS

| EP | 0884115 | 12/1998 |
|----|---------|---------|
| JP | 2008173399 | 7/2008 |

OTHER PUBLICATIONS

PCT/NL2009/050773 International Search Report, mailed Mar. 19, 2010.

*Primary Examiner* — Gregory J Toatley
*Assistant Examiner* — Jarreas C Underwood
(74) *Attorney, Agent, or Firm* — Waddey & Patterson, P.C.; Rebecca M. Barnett

(57) ABSTRACT

Method and system for inspecting the inside of a small channel, e.g. a flexible tube or hose, particularly for medical use, e.g. included in an endoscope, for the presence of inside contaminations on the wall of the tube, comprising providing the inside of the channel with a liquid having a refractive index which is higher than the refractive index of the channel wall, transmitting a signal into one end of the channel having a wavelength w, comparing the spectrum of the signal received at the other end of the channel with the wavelength w of the transmitted signal and determining, e.g. by a spectrum analyzer, whether the latter signal contains any wavelength w' which is unequal to the wavelength w of the transmitted signal, and indicating that, when not any wavelength w' is determined unequal to w, the channel is not contaminated or that, when any wavelength w' is determined unequal to w, the channel is contaminated. The system may include means for cleaning the inside of the channel by means of said liquid having a refractive index which can be higher than the refractive index of the channel wall which thus is used both as cleaning liquid and as light conducting core.

14 Claims, 2 Drawing Sheets

(56) References Cited

U.S. PATENT DOCUMENTS

Figure 1:
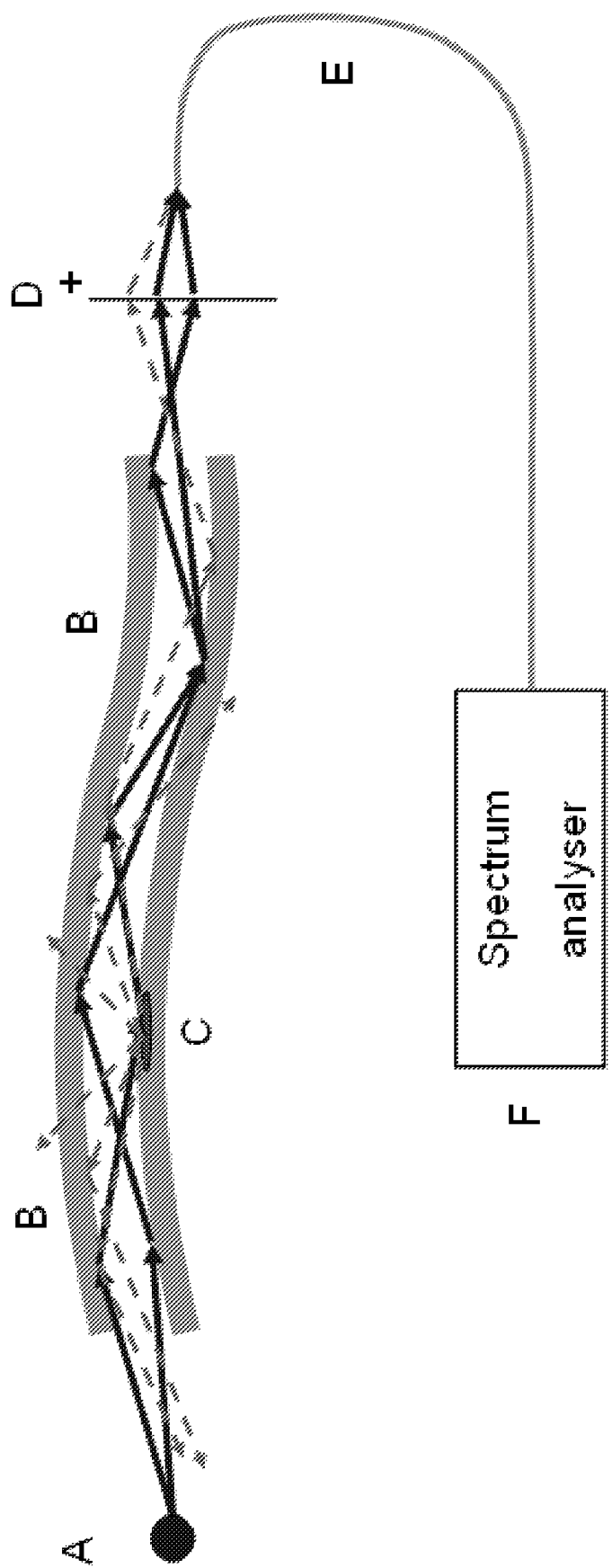

| | | | |
|---|---|---|---|
| 5,922,958 A * | 7/1999 | Schugt | 73/596 |
| 6,385,380 B1 | 5/2002 | Friedrich et al. | |
| 6,704,666 B2 * | 3/2004 | Normen | 702/45 |
| 7,246,627 B2 * | 7/2007 | Jacobs et al. | 134/113 |
| 7,358,476 B2 * | 4/2008 | Kiesel et al. | 250/208.2 |
| 7,948,621 B2 * | 5/2011 | Burns et al. | 356/338 |

* cited by examiner

METHOD FOR INSPECTING THE INSIDE OF A NARROW HOSE OR TUBE PARTICULARLY FOR MEDICAL USE

The present invention refers to a method for inspecting the inside of a narrow channel or hollow instrument, e.g. a flexible tube or hose, particularly for medical use, e.g. included in an endoscope, for the presence of inside contaminations. Hereinafter the channel may also be indicated as tube or hose.

Public health organisations have observed that effectiveness of cleaning and disinfection of flexible endoscopes is difficult to ensure, which results in numerous incidents. The current practice in fact is relying on thoroughly qualified cleaning methods and equipment, complemented by a number of tests. However, none of these tests proves that an instrument has been effectively cleaned. Human errors and/or equipment failure can cause contaminations inside the tube which remain unnoticed, resulting in infection of the patient. The most common practice is monitoring of the various parameters of the cleaning process, e.g. the concentration of the detergent and disinfectant and the flow speed of the cleaning fluid. Another existing way to inspect the effectivity of the cleaning process is the helix test, which test the penetration of steam into instrument cavities. While some cases of equipment malfunctioning can be detected in this way, cleaning performance is not measured. An albumin test can be used to test whether a cleaning method or equipment is suitable for cleaning of an endoscope. However, since the endoscope is contaminated by the test, this method can not be used for routine inspection after cleaning. Alternatively, laboratory testing of the rinsing fluid or another sample can be done after cleaning. However, this approach is too time consuming for routine inspection.

One aim of the method according to the invention is to provide a method and means for efficient and effective internal inspection of endoscope channels and other tubing and flexible hoses or hollow instruments, etc.

The method according to the invention aims to provide more efficiency and reliability in the use of endoscopes etc. To that end, the method includes next steps:
- providing the inside of the channel with a liquid having a refractive index which is higher than the refractive index of the channel wall;
- transmitting an (optical) signal ("light") into one end of the channel having a wavelength w;
- determining if the signal received at the other end of the channel contains any wavelength w' which is unequal to the wavelength w of the transmitted signal;
- concluding that when the intensity of the signal with a wavelength w' exceeds a threshold, the tube is contaminated or when the intensity of the signal with a wavelength w' does not exceed a threshold, the tube is not contaminated.

By filling the channel with a liquid having a refractive index which is higher than the refractive index of the channel wall, the channel plus liquid can be temporarily used as a "liquid core optical waveguide".

For example, the channel wall comprises a fluoropolymer and the liquid is water or an organic solvent, e.g. ethanol. The signal transmitted into the one end of the channel is preferred to have a wavelength w which corresponds to blue or UV light. The wavelength spectrum of the signal received at the other end of the channel may be analyzed by means of an optical spectrum analyzer.

A system arranged for performing the method according to the invention preferably comprises means for providing the inside of the channel with a liquid having a refractive index which is higher than the refractive index of the channel wall, a device for transmitting a signal into one end of the channel having a wavelength w, a device for comparing the spectrum of the signal received at the other end of the channel with the wavelength w of the transmitted signal and determining whether the latter signal contains any wavelength w' which is unequal to the wavelength w of the transmitted signal, and indication means which indicate that, when not any wavelength w' is determined unequal to w, the channel is not contaminated or that, when any wavelength w' is determined unequal to w, the channel is contaminated.

It may be preferred to include or integrate the system in/with a system for cleaning the inside of the channel by means of the liquid having a refractive index which is higher than the refractive index of the channel wall is also used as cleaning liquid.

Liquid core optical waveguide are known in the art as a means to transport light or to do optical measurements on the liquid inside the wave guide such that a long optical path through the liquid is realised with a small amount of liquid. Examples of the known art are WO0039615, WO9512138 and U.S. Pat. No. 6,385,380.

One aspect of the present invention is to temporarily convert a narrow channel, tube or hose, which is not designed or, in normal operation, used as a waveguide, into a liquid core optical waveguide, thus allowing inspection of the inside of the tube for contamination. After inspection, the tube can be used again for its normal purpose.

Advantageous of the present method is that the channel may be bent and that (only) one or both extremities of the tube need to be accessible. Moreover, the method allows routine, non-destructive inspection of non-accessible tubes, replacement of which is time consuming and/or expensive.

Hereinafter the method will be discussed more in detail referring to some figures which illustrate exemplary configurations which is arranged to perform the method.

Figure 2:
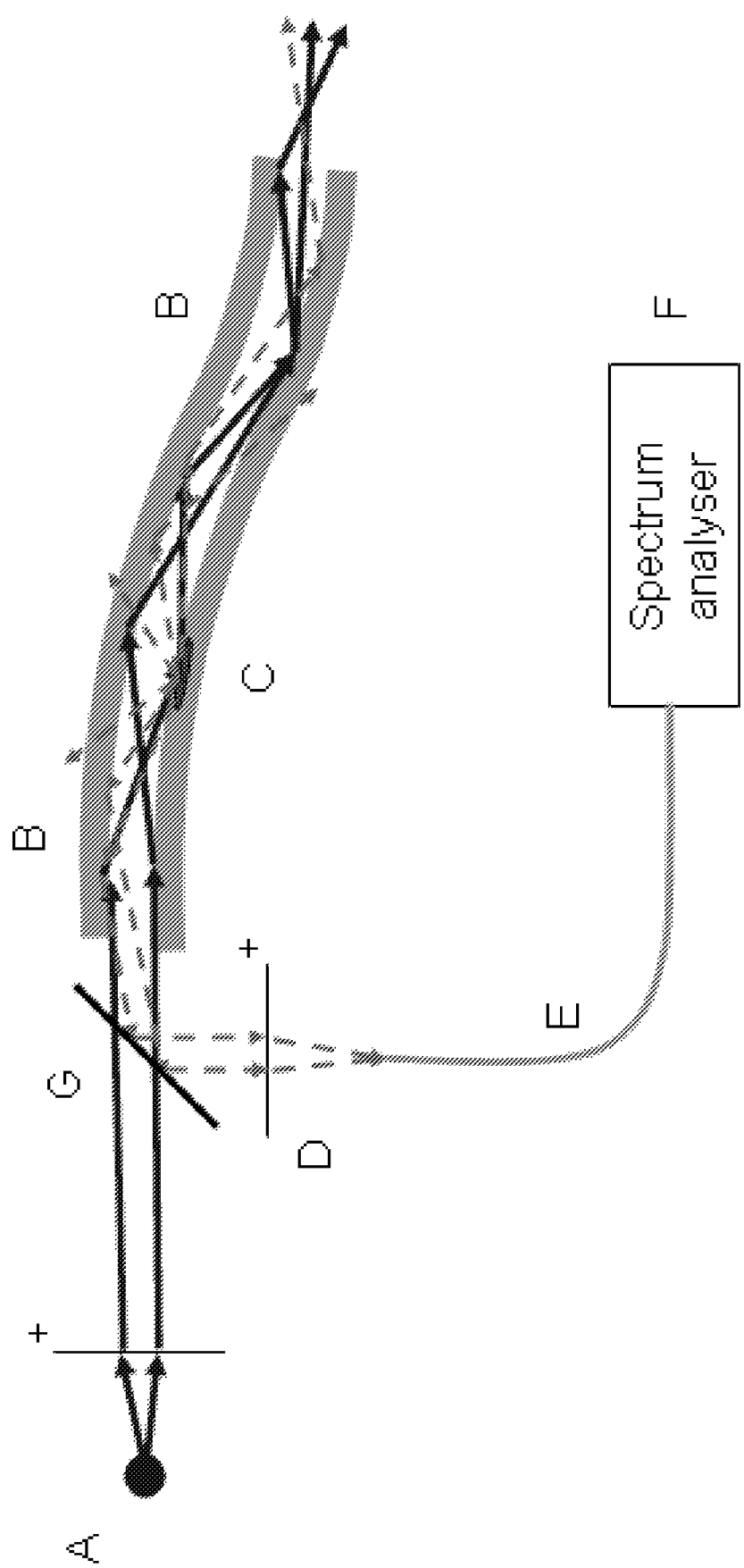

FIG. 1 shows a first exemplary configuration;
FIG. 2 shows a second exemplary configuration.

In the figure the following reference signs are used:
A Light source
B Channel
C Contamination spot
D Optical detector
E Fibre
F Spectrum analyser
G Beam splitter minor FIG. 1 shows a light source A, e.g. a UV LED or a UV laser which is optically connected to one open extreme of an endoscope channel B which has to be inspected whether it contains contaminations at its interior or not. The other open extreme of the channel B is optically connected to an optical collector or detector D, which is connected, possibly via a fibre E to a spectrum analyser F. The inside of the channel is provided with a liquid having a refractive index which is higher than the refractive index of the channel wall, which causes the channel to behave like a "liquid core optical waveguide".

If the channel B is clean, the spectrum of the output signal, received by de detector D and supplied to the analyser F, will be equal to the spectrum of the light source A. However, if the channel contains e.g. contamination C, this contamination will cause the optical signal to include one or more wavelengths having wavelength than the wavelength of the originating light source A. So, if such another, e.g. longer, wavelength is detected by the spectrum analyser F, this indicates the presence of contamination inside the channel B In an alternative exemplary embodiment, illustrated in FIG. 2, light caused by the presence of contamination is detected via a beam splitter minor G at the same extremity as the light source A. The advantage is that access to one extremity of the channel is sufficient, which may be easier in operation.

In this way the method for inspecting the inside of a small channel B, for the presence of inside contaminations, can be performed, viz. by providing the inside of the channel with a liquid, e.g. water based solution or an organic solvent, having a refractive index which is higher than the refractive index of the channel wall, transmitting a signal, e.g. in the blue or UV optical area, into one end of the channel having a wavelength w, determining if the signal received at the other end of the channel contains any wavelength w' which is unequal to the wavelength w of the transmitted signal and, finally, concluding that when the intensity of light with a wavelength s' is higher/lower than a certain threshold, the tube is contaminated/clean.

Determination of inside channel contamination may be included or integrated in a system for cleaning the inside of the channel by means of a (flowing) liquid, which liquid, if having a refractive index which is higher than the refractive index of the channel wall, can simultaneously act for light guiding in the channel, acting as "liquid core optical waveguide".

While specific embodiments have been described above, it will be appreciated that the invention may be practiced otherwise than as described. Moreover, specific items discussed with reference to any of the Figures may freely be interchanged supplementing each outer in any particular way. For example, the term 'narrow channel' may also be construed as a hollow structure. The descriptions above are intended to be illustrative, not limiting. Thus, it will be apparent to one skilled in the art that modifications may be made to the invention as described in the foregoing without departing from the scope of the claims set out below.

The invention claimed is:

1. A method for inspecting the inside of a narrow channel for the presence of inside contaminations, comprising the following steps:
    providing the inside of the channel with a liquid having a refractive index which is higher than the refractive index of a channel wall or at least of an innermost channel wall layer;
    transmitting a signal having a wavelength w into a first end of the channel;
    determining if a signal received at a second end of the channel contains any wavelength w' which is unequal to the wavelength w of the transmitted signal;
    concluding that when the intensity of the signal with a wavelength w' exceeds a threshold, the tube is contaminated or when the intensity of the signal with a wavelength w' does not exceed a threshold, the tube is not contaminated.

2. The method of claim 1, wherein the channel or the innermost channel wall layer comprises a fluoropolymer and further wherein the liquid is an aqueous solution.

3. The method of claim 1, wherein the channel wall or the innermost channel wall layer comprises a fluoropolymer and further wherein the liquid is an organic solvent.

4. The method of claim 1, wherein the signal transmitted into the first end of the channel has a wavelength w which corresponds to the wavelength of blue or UV light.

5. The method of claim 1, wherein a wavelength spectrum of the signal received at the second end of the channel is analyzed by a spectrum analyzer.

6. The method of claim 1, including a step for cleaning the inside of the channel with a liquid, said liquid having a refractive index higher than the refractive index of the channel wall.

7. The method of claim 1, wherein different wavelengths identify different types of contamination.

8. The method of claim 1, wherein the channel is rinsed with a fluid causing the contaminated channel and/or the contaminations within the channel to produce light with a wavelength w'.

9. The method according to claim 1, wherein the narrow channel is a hollow instrument.

10. A system for inspecting the inside of a small channel for the presence of inside contaminations, comprising
    means for providing the inside of the channel with a liquid having a refractive index which is higher than the refractive index of a channel wall or at least an innermost channel wall layer,
    a device for transmitting a signal having a wavelength w into a first end of the channel,
    a device for determining whether a spectrum of a signal received at a second end of the channel contains any wavelength w' which is unequal to the wavelength w of the transmitted signal;
    indication means which indicate that, when any wavelength w' is determined unequal to the wavelength w of the transmitted signal, the channel is not contaminated or that, when any wavelength w' is determined unequal to the wavelength w of the transmitted signal, the channel is contaminated.

11. The system of claim 10, wherein the signal transmitted into the first end of the channel has a wavelength w which corresponds to blue or UV light.

12. The system of claim 10, wherein the device for determining whether the spectrum of the signal received at the second end of the channel contains any wavelength w' which is unequal to the wavelength w of the transmitted signal is a wave or spectrum analyzer.

13. The system of claim 10, wherein the system is included in or integrated with a system for cleaning the inside of the channel by means of a liquid, said liquid having a refractive index which is higher than the refractive index of the channel wall or at least of an innermost channel wall layer.

14. A system according to claim 10, wherein the small channel is a hollow instrument.

* * * * *

UNITED STATES PATENT AND TRADEMARK OFFICE
CERTIFICATE OF CORRECTION

PATENT NO.       : 8,593,626 B2                                          Page 1 of 1
APPLICATION NO. : 13/139970
DATED            : November 26, 2013
INVENTOR(S)      : Egbert Anne Martijn Brouwer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 340 days.

Signed and Sealed this

Twenty-second Day of September, 2015

Michelle K. Lee
*Director of the United States Patent and Trademark Office*